(12) United States Patent
Joung et al.

(10) Patent No.: US 12,292,401 B2
(45) Date of Patent: May 6, 2025

(54) WELD PORTION INSPECTION METHOD USING THERMAL IMAGE SENSING

(71) Applicant: LG ENERGY SOLUTION, LTD., Seoul (KR)

(72) Inventors: Mun Chae Joung, Daejeon (KR); Hang June Choi, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 708 days.

(21) Appl. No.: 17/619,975

(22) PCT Filed: Oct. 21, 2020

(86) PCT No.: PCT/KR2020/014365
§ 371 (c)(1),
(2) Date: Dec. 16, 2021

(87) PCT Pub. No.: WO2021/107407
PCT Pub. Date: Jun. 3, 2021

(65) Prior Publication Data
US 2022/0357294 A1    Nov. 10, 2022

(30) Foreign Application Priority Data
Nov. 27, 2019  (KR) ........................ 10-2019-0153866

(51) Int. Cl.
*G01N 25/72* (2006.01)
*B23K 31/12* (2006.01)
*H01M 10/48* (2006.01)

(52) U.S. Cl.
CPC ........... *G01N 25/72* (2013.01); *B23K 31/125* (2013.01); *H01M 10/486* (2013.01)

(58) Field of Classification Search
CPC .. B23K 2101/38; B23K 31/125; G01N 25/72; G01N 33/207; H01M 10/4285; H01M 50/516; H01M 10/486; Y02E 60/10
USPC ........................................ 324/456, 452, 463
See application file for complete search history.

(56) References Cited

U.S. PATENT DOCUMENTS

| 8,802,253 B2 | 8/2014 | Stancu et al. | |
| 2007/0047796 A1 | 3/2007 | Anantharaman | |
| 2009/0087083 A1 | 4/2009 | Anantharaman | |
| 2011/0256430 A1* | 10/2011 | Stancu ................ | B23K 31/125 429/50 |

(Continued)

FOREIGN PATENT DOCUMENTS

| CN | 102686355 A | 9/2012 |
| CN | 103339736 A | 10/2013 |

(Continued)

OTHER PUBLICATIONS

Extended European Search Report for European Application No. 20891574.4, dated Jul. 22, 2022.

(Continued)

*Primary Examiner* — Giovanni Astacio-Oquendo
(74) *Attorney, Agent, or Firm* — Birch, Stewart, Kolasch & Birch, LLP

(57) ABSTRACT

Disclosed is a weld portion inspection method using thermal image sensing, wherein the method includes heating the weld portion using Joule heat; and determining whether the weld portion is defective based on a temperature increase pattern of the weld portion by the heating.

10 Claims, 5 Drawing Sheets

(56) References Cited

U.S. PATENT DOCUMENTS

| | | | |
|---|---|---|---|
| 2015/0236386 A1 | 8/2015 | Yang et al. | |
| 2020/0020998 A1 | 1/2020 | Kwon et al. | |
| 2022/0311102 A1* | 9/2022 | Cournoyer | B23K 31/125 |
| 2023/0009074 A1* | 1/2023 | Kim | B23K 31/125 |

FOREIGN PATENT DOCUMENTS

| | | | |
|---|---|---|---|
| CN | 109540967 A | 3/2019 | |
| JP | 8-122051 A | 5/1996 | |
| JP | 2000-131254 A | 5/2000 | |
| JP | 2000-258356 A | 9/2000 | |
| JP | 3271861 B2 | 4/2002 | |
| JP | 2008-145252 A | 6/2008 | |
| JP | 4140218 B2 | 8/2008 | |
| JP | 4884472 B2 | 2/2012 | |
| JP | 4983236 B2 | 7/2012 | |
| KR | 10-2008-0109947 A | 12/2008 | |
| KR | 20080109947 A * | 12/2008 | G01N 25/72 |
| KR | 10-2011-0115967 A | 10/2011 | |
| KR | 10-2014-0020660 A | 2/2014 | |
| KR | 10-1887148 B1 | 8/2018 | |
| KR | 10-2023722 B1 | 9/2019 | |
| WO | WO 2018/074161 A1 | 4/2018 | |
| WO | WO 2019/107722 A1 | 6/2019 | |

OTHER PUBLICATIONS

International Search Report for PCT/KR2020/014365 (PCT/ISA/210) mailed on Jan. 15, 2021.

Ishikawa et al., "Detecting deeper defects using pulse phase thermography", Infrared Physics & Technology 57 (2013), pp. 42-49.

\* cited by examiner

[FIG. 1]
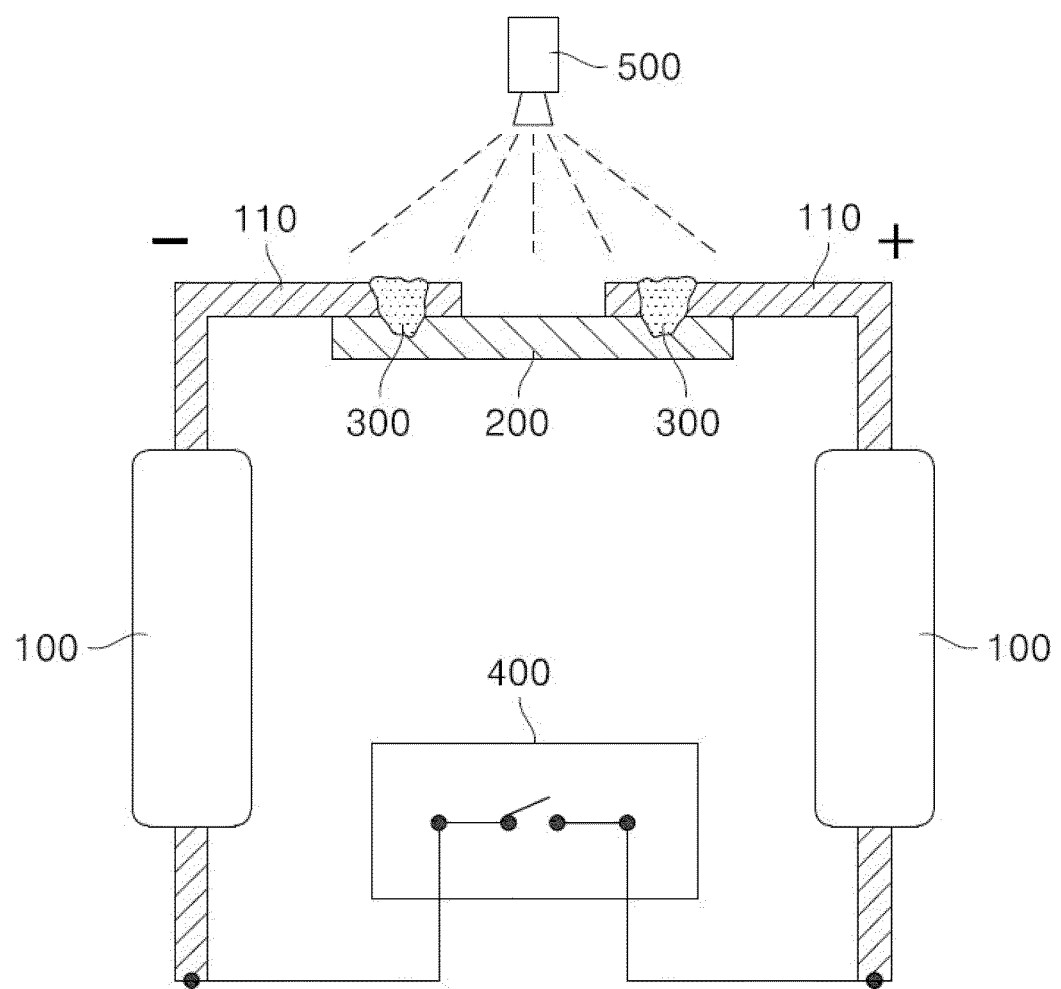

[FIG. 2]
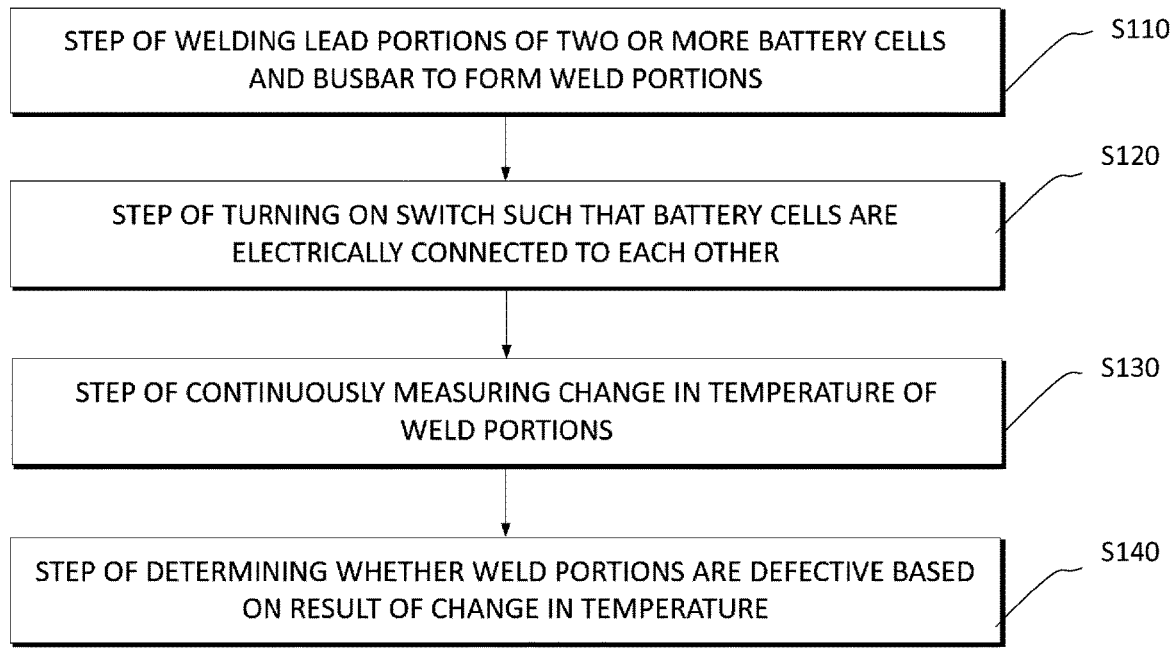

【FIG. 3】
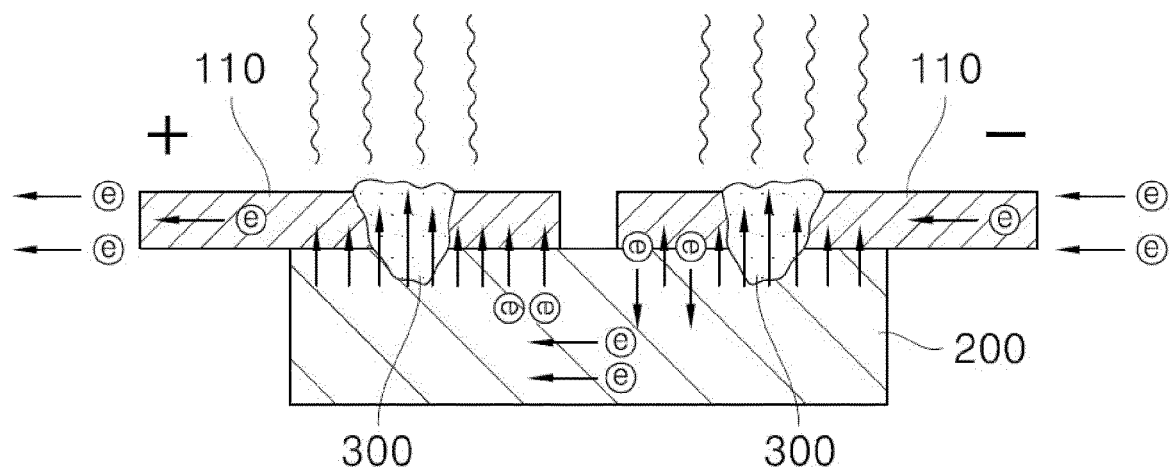
【FIG. 4】
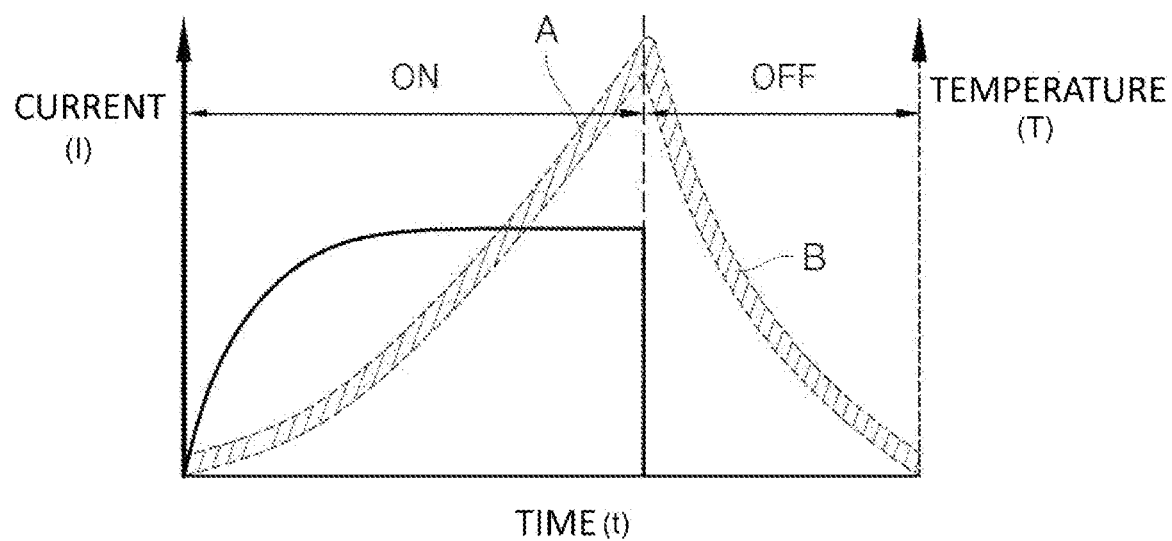

【FIG. 5】
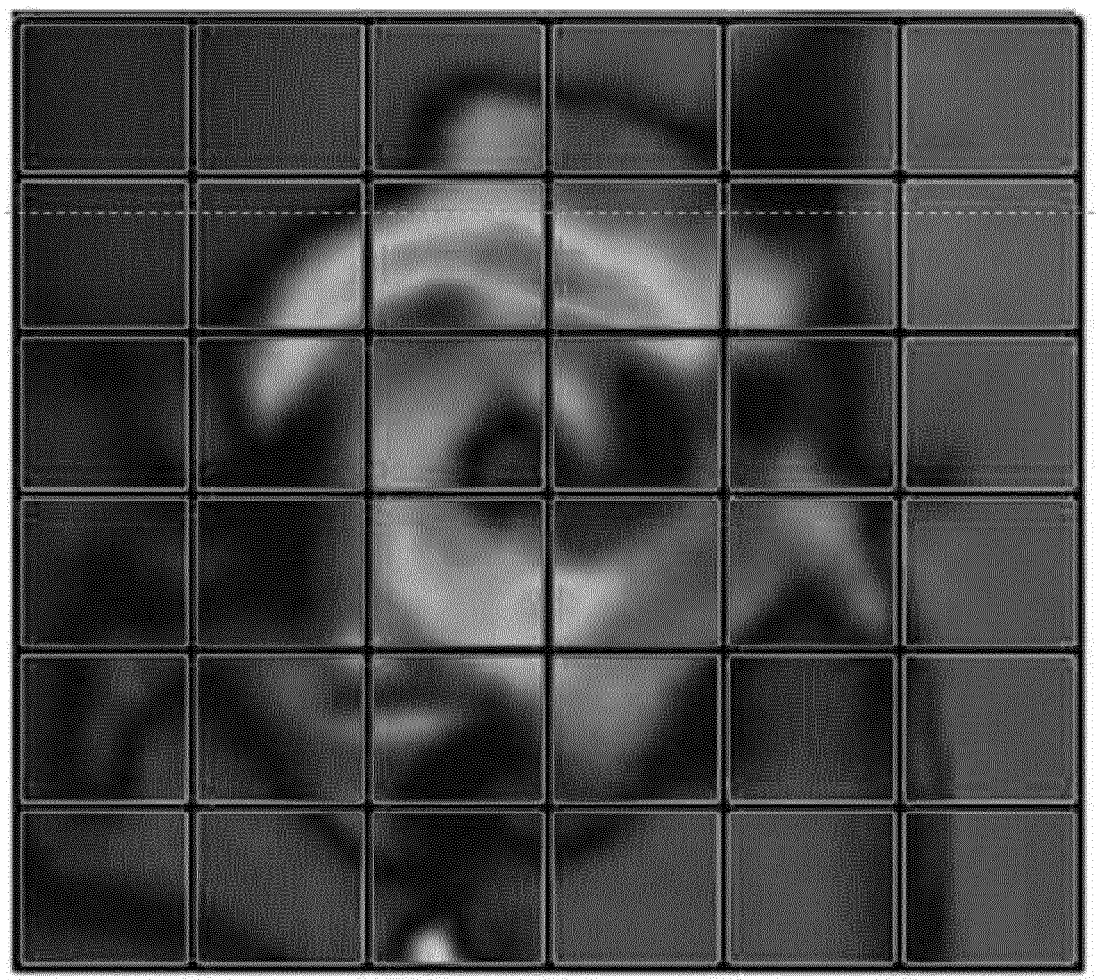

[FIG. 6]
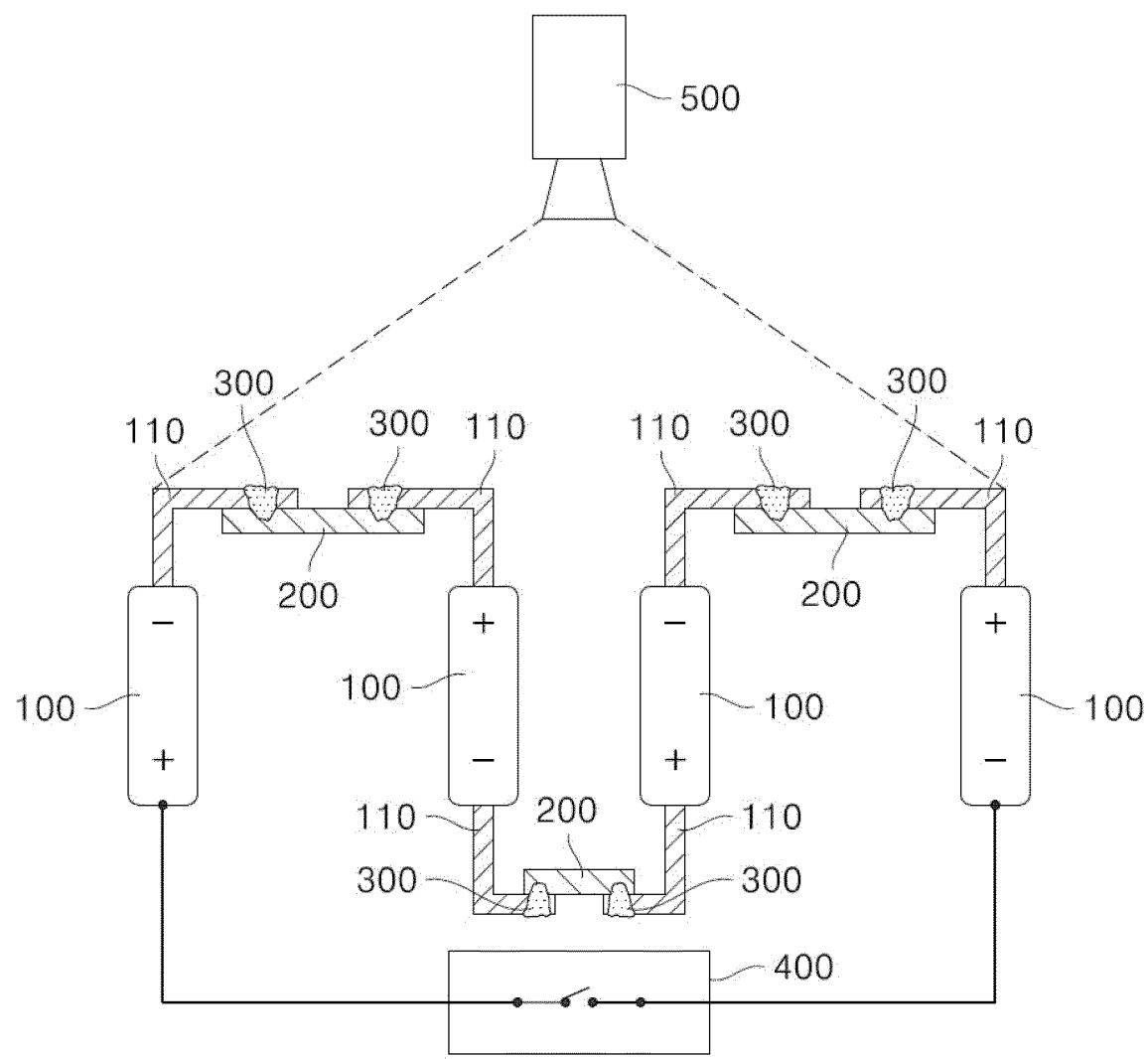

WELD PORTION INSPECTION METHOD USING THERMAL IMAGE SENSING

TECHNICAL FIELD

This application claims the benefit of priority to Korean Patent Application No. 2019-0153866 filed on Nov. 27, 2019, the disclosure of which is hereby incorporated by reference herein its entirety.

The present invention relates to a weld portion inspection method using thermal image sensing, and more particularly to a weld portion inspection method using thermal image sensing capable of sensing temperature increase and decrease patterns of a weld portion through thermal images and determining whether the weld portion is defective based on the result of analysis thereof.

BACKGROUND ART

With technological development of mobile devices, such as mobile phones, laptop computers, camcorders, and digital cameras, and an increase in demand therefor, research on secondary batteries, which are capable of being charged and discharged, has been actively conducted. In addition, secondary batteries, which are energy sources substituting for fossil fuels causing air pollution, have been applied to an electric vehicle (EV), a hybrid electric vehicle (HEV), and a plug-in hybrid electric vehicle (P-HEV), and therefore there is an increasing necessity for development of secondary batteries.

There are a nickel-cadmium battery, a nickel-hydride battery, a nickel-zinc battery, and a lithium secondary battery as currently commercialized secondary batteries. Thereamong, the lithium secondary battery is in the spotlight, since the lithium secondary battery has little memory effect, whereby the lithium secondary battery is capable of being freely charged and discharged, has a very low self-discharge rate, and has high energy density, compared to the nickel-based secondary batteries.

Meanwhile, several battery cells are disposed in a secondary battery used in small-sized devices, whereas a battery module including a plurality of battery cells electrically connected to each other is used in vehicles. Since the plurality of battery cells is connected to each other in series and in parallel, the capacity and output of the battery module are increased. A busbar is used for electrical connection between the battery cells.

The busbar and leads of the battery cells are generally connected to each other by welding, since each of the busbar and the leads is an electrically conductive metal.

Conventionally, there is no technology for detecting all weld defects, such as poor welding and overwelding, at the time of welding therebetween, and therefore improvement in weld quality is limited. That is, in the case in which macrography is performed after resistance welding, partial detection of overwelding is possible, but detection of poor welding is impossible. For stick inspection, in which a welded portion is pulled in order to detect non-welding, partial detection of poor welding or detection of non-welding is possible. In this case, however, force is directly applied to a lead or a busbar, whereby a battery cell may be damaged.

Japanese Patent Application Publication No. 2000-131254 discloses technology related to a tab terminal member and a pattern portion of a busbar, which are two metal members welded to each other, the technology being capable of holding the front end of the tab terminal member using a heating jig, transferring heat from the tab terminal member to the pattern portion of the busbar via a weld portion to measure the maximum temperature or temperature distribution at the rear surface of the pattern portion of the busbar using a radiation thermometer, and comparing the measured maximum temperature or the area of a region having a predetermined temperature or higher with a comparative value obtained in advance to determine whether the weld portion is defective.

The prior art document has an advantage in that it is possible to somewhat determine whether the weld portion is defective without destroying the weld portion. However, separate equipment and power for heat transfer are necessary. As a result, there is a problem in that an inspection apparatus may be complicated and inspection cost based thereon may be increased.

PRIOR ART DOCUMENT (Patent Document 1) Japanese Patent Application Publication No. 2000-131254

DISCLOSURE

Technical Problem

The present invention has been made in view of the above problems, and it is an object of the present invention to provide a weld portion inspection method capable of accurately determining whether a weld portion is defective.

It is another object of the present invention to provide a weld portion inspection method capable of determining whether a weld portion is defective without separate external electric power.

It is a further object of the present invention to provide a weld portion inspection method using simple equipment.

Technical Solution

In order to accomplish the above objects, the present invention provides a method of inspecting a weld portion between a lead portion of a battery cell and a busbar, wherein the weld portion (300) is heated using Joule heat and whether the weld portion (300) is defective is determined based on a temperature increase pattern of the weld portion (300).

Also, in the method of inspecting the weld portion between the lead portion of the battery cell and the busbar according to the present invention, the Joule heat may be generated by current supplied from the battery cell (100) welded to the busbar (200).

Also, in the method of inspecting the weld portion between the lead portion of the battery cell and the busbar according to the present invention, the battery cell (100) may be in a packed state before shipment.

Also, in the method of inspecting the weld portion between the lead portion of the battery cell and the busbar according to the present invention, the heated weld portion (300) may be cooled and whether the weld portion (300) is defective may be determined based on a temperature decrease pattern of the weld portion (300).

Also, in the method of inspecting the weld portion between the lead portion of the battery cell and the busbar according to the present invention, the cooling may be performed by interrupting the supply of current from the battery cell (100).

Also, in the method of inspecting the weld portion between the lead portion of the battery cell and the busbar according to the present invention, the temperature increase pattern may be at least one of a time taken until the temperature reaches a specific temperature, a temperature increase rate over time, and the maximum temperature.

Also, in the method of inspecting the weld portion between the lead portion of the battery cell and the busbar according to the present invention, the temperature decrease pattern may be at least one of a time taken until the temperature reaches an initial temperature from a predetermined temperature and a temperature decrease rate over time.

Also, in the method of inspecting the weld portion between the lead portion of the battery cell and the busbar according to the present invention, the temperature increase pattern and/or the temperature decrease pattern may be set for the weld portion and a neighboring region of the weld portion, the weld portion and the neighboring region of the weld portion being divided into a predetermined number of regions.

Also, the method of inspecting the weld portion between the lead portion of the battery cell and the busbar according to the present invention may include a first step of welding lead portions (110) of two or more battery cells (100) and a busbar (200) to form weld portions (300), a second step of turning on a switch such that the battery cells (100) are electrically connected to each other, a third step of continuously measuring a change in temperature of each of the weld portions (300), and a fourth step of determining whether each of the weld portions (300) is defective based on the result of change in temperature.

Also, in the method of inspecting the weld portion between the lead portion of the battery cell and the busbar according to the present invention, the second step may be maintained for a predetermined time after the battery cells (100) are discharged.

Also, in the method of inspecting the weld portion between the lead portion of the battery cell and the busbar according to the present invention, the third step may be performed until the battery cells (100) are discharged.

Advantageous Effects

A weld portion inspection method using thermal image sensing according to the present invention has an advantage in that whether a weld portion is defective is determined in simultaneous consideration of heat generation characteristics and cooling characteristics of the weld portion, whereby more accurate determination is possible.

In addition, the weld portion inspection method using thermal image sensing according to the present invention has an advantage in that electric power of a battery cell itself to be inspected is used, whereby no separate electric power is necessary and furthermore it is possible to minimize incidental equipment for inspection.

DESCRIPTION OF DRAWINGS

FIG. 1 is a view showing a configuration for weld portion inspection according to a first preferred embodiment of the present invention.

FIG. 2 is a flowchart illustrating a weld portion inspection method according to a first preferred embodiment of the present invention.

FIG. 3 is a conceptual view illustrating a heat generation mechanism of a weld portion at the time of current application.

FIG. 4 is a conceptual view illustrating a change in temperature of a weld portion at the time of current application or interruption.

FIG. 5 is a view showing an example of the temperature distribution image result in a neighboring region including a weld portion.

FIG. 6 is a view showing a configuration for weld portion inspection according to a second preferred embodiment of the present invention.

BEST MODE

In the present application, it should be understood that the terms "comprises," "has," "includes," etc. specify the presence of stated features, numbers, steps, operations, elements, components, or combinations thereof, but do not preclude the presence or addition of one or more other features, numbers, steps, operations, elements, components, or combinations thereof.

In addition, the same reference numbers will be used throughout the drawings to refer to parts that perform similar functions or operations. In the case in which one part is said to be connected to another part in the specification, not only may the one part be directly connected to the other part, but also, the one part may be indirectly connected to the other part via a further part. In addition, that a certain element is included does not mean that other elements are excluded, but means that such elements may be further included unless mentioned otherwise.

Hereinafter, a weld portion inspection method using thermal image sensing according to the present invention will be described.

FIG. 1 is a view showing a configuration for weld portion inspection according to a first preferred embodiment of the present invention. Referring to FIG. 1, a lead portion 110 extending from each of two battery cells 100, a busbar 200 configured to electrically connect the lead portions 110 to each other, a weld portion 300 configured to fix each lead portion 110 and the busbar 200 to each other, and a thermal imaging camera 500 configured to measure a change in temperature of the weld portion 300 are provided.

The two battery cells 100 are cells to be inspected in order to determine various kinds of performance, such as performance related to the weld portions, for product shipment. One side of the busbar 200 is connected to a negative electrode lead extending from one of the battery cells 100 and the other side of the busbar 200 is connected to a positive electrode lead extending from the other battery cell 100, whereby the battery cells 100 may be electrically connected to each other.

In general, each lead portion 110 and the busbar 200, which are made of metals, are connected to each other by welding, such as resistance welding. At this time, the weld portion 300 is formed so as to extend from the lead portion 110 to the busbar 200.

Meanwhile, a switch 400 is provided between lead portions of the battery cells 100 that are not connected to the busbar 200, i.e. between a positive electrode lead of the battery cell 100 located on the left side of FIG. 1 and a negative electrode lead of the battery cell 100 located on the right side of FIG. 1. The switch is configured to perform electrical connection or interruption therebetween.

In addition, the thermal imaging camera 500 is installed in the vicinity of the weld portions 300, each of which fixes a corresponding one of the lead portions 110 and the busbar 200 to each other. The thermal imaging camera is a camera configured to track and detect heat and to express the heat using different colors based on the temperature thereof, which is technology well known in various fields, and therefore a detailed description of the operating principle or the function thereof will be omitted.

Hereinafter, a weld portion inspection method will be described based on the configuration for weld portion inspection shown in FIG. 1. FIG. 2 is a flowchart illustrating a weld portion inspection method according to a first preferred embodiment of the present invention, FIG. 3 is a conceptual view illustrating a heat generation mechanism of a weld portion at the time of current application, FIG. 4 is a conceptual view illustrating a change in temperature of a weld portion at the time of current application or interruption, and FIG. 5 is a view showing an example of the temperature distribution image result in a neighboring region including a weld portion.

The weld portion inspection method according to the present invention includes a first step (S110) of welding lead portions 110 of two or more battery cells 100 and a busbar 200 to form weld portions 300, a second step (S120) of turning on a switch such that the battery cells 100 are electrically connected to each other, a third step (S130) of continuously measuring a change in temperature of each of the weld portions 300, and a fourth step (S140) of determining whether each of the weld portions 300 is defective based on the result of change in temperature.

The first step was described in detail with reference to FIG. 1, and therefore a duplicate description thereof will be omitted.

The second step is a step of turning on the switch 400 such that the battery cells 100 are electrically connected to each other. At this time, heat is generated from each weld portion 300.

In connection with heat generation, as shown in FIG. 3, electrons e supplied from a negative electrode terminal of one of the battery cells 100 move to a positive electrode terminal of the other battery cell 100 via the busbar 200. At this time, Joule heat represented by Equation 1 is generated in each weld portion 300 due to resistance caused by coupling between dissimilar metals and a change in structure thereof.

$$Q = I^2 \times R \times t \quad \text{Equation 1)}$$

Here, Q indicates Joule heat, I indicates current, R indicates resistance, and t indicates time.

Meanwhile, it is preferable to use electric power of the battery cells directly connected to the busbar 200, although a separate external power source may be used as a power source configured to generate Joule heat in each weld portion 300.

In general, a battery cell 100 is completed through an activation step after injection of an electrolytic solution. At this time, the battery cell 100 is charged with a predetermined amount of electric power, and therefore it is advantageous to use the electric power. That is, at the time of using an external power source, not only is a separate power source needed but also additional wiring for electrical connection between the external power source and the bus bar 200 is needed. In contrast, it is possible to overcome the above problem in the case in which electric power charged in the battery cells 100 connected to the bus bar 200 is used.

When current charged in each battery cell 100 flows out, as shown in FIG. 4, the temperature of the weld portion 300 is increased due to heat generation as current application time is increased. When the battery cell 100 is discharged, no more current flows, whereby the temperature of the weld portion 300 is decreased.

The third step, which is a step of measuring a change in temperature of each of the weld portions 300, may be performed simultaneously with the second step of electrically connecting the battery cells 100 to each other.

In order to measure the change in temperature, thermal radiation energy in the vicinity of the weld portion 300 is electronically scanned using the thermal imaging camera 500 to create temperature distribution data for each position based on current application time.

That is, as shown in FIG. 5, the temperature of the surroundings including the weld portion is distributed to a plurality of unit regions, and temperature data for each region are secured.

Finally, in the fourth step, which is a step of determining whether each of the weld portions 300 is defective based on the result of change in temperature, whether the change in temperature is within a normal range is determined by comparison.

As an example, referring to FIG. 4, in the case in which a temperature value measured when current flows is increased within a normal range (region A of FIG. 4), it is determined that the weld portion 300 is normally welded. In contrast, in the case in which the temperature value is increased while deviating from the normal range, it is determined that the weld portion 300 is defective.

In addition, the heated weld portion 300 is left to be cooled down for a predetermined time after the battery cell 100 is completely discharged. In the same manner, whether a temperature decrease pattern of the measured weld portion 300 is changed within a normal range (region B of FIG. 4) is determined by comparison in order to determine whether the weld portion is defective.

Temperature increase occurs as inner heat accumulates within a short time by forced heating due to current application whereas cooling is a phenomenon in which the accumulated heat is naturally transmitted to the inside/outside.

Particularly, in the cooling process, convection, radiation, and internal conduction through a surface may have different cooling patterns depending on the internal structure of the weld portion, such as the surface state, pores, grain size, and forming structure of the weld portion. Consequently, it is possible to determine the state of the weld portion based on a temperature decrease pattern at the time of cooling.

Meanwhile, a concrete example of the temperature increase pattern may be time taken until the temperature reaches a specific temperature, a temperature increase rate (change in temperature/time), or the maximum temperature. In addition, the cooling pattern may be time taken until the temperature reaches the original temperature from the maximum temperature or a temperature decrease rate (change in temperature/time).

In a concrete example of each of the temperature increase pattern and the cooling pattern, it is preferable to simultaneously utilize a single factor or a plurality of factors. In particular, it is more preferable to apply the factors to all of the plurality of divided regions as shown in FIG. 5.

Of course, it is obvious that the temperature change distribution result of the weld portion is matched together with macrography and stick inspection, which are generally performed to detect weld defects, in order to secure the temperature change result of the weld portion in a normal state.

FIG. 6 is a view showing a configuration for weld portion inspection according to a second preferred embodiment of the present invention.

The second embodiment is identical to the first embodiment except that four battery cells 100 are connected to each other in series and that three busbars 200 are used in order to electrically connect neighboring ones of the battery cells 100 to each other.

That is, a switch 400 is connected such that current flows, weld portions 300 formed in each busbar 200 are scanned using a thermal imaging camera 500, and temperature data are analyzed, whereby it is possible to determine whether weld portions 300 formed in a specific busbar 200 are defective.

Although a single thermal imaging camera 500 is shown as being used in the figure, a plurality of thermal imaging cameras 500 may be used.

Although the specific details of the present invention have been described in detail, those skilled in the art will appreciate that the detailed description thereof discloses only preferred embodiments of the present invention and thus does not limit the scope of the present invention. Accordingly, those skilled in the art will appreciate that various changes and modifications are possible, without departing from the category and the technical idea of the present invention, and it will be obvious that such changes and modifications fall within the scope of the appended claims.

DESCRIPTION OF REFERENCE NUMERALS

100: Battery cell
110: Lead portion
200: Busbar
300: Weld portion
400: Switch
500: Thermal imaging camera

The invention claimed is:

1. A method of inspecting a weld portion between a lead portion of a battery cell and a busbar, the method comprising:
   a first operation of welding lead portions of two or more battery cells including the battery cell and the busbar to form weld portions that include the weld portion;
   a second operation of turning on a switch connected to the two or more battery cells such that the two or more battery cells are electrically connected to each other;
   a third operation of heating the weld portion using Joule heat and continuously measuring a change in temperature over time of the weld portion; and
   a fourth operation of determining whether the weld portion is defective based on a temperature increase pattern of the weld portion obtained from the continuously measuring of the change in the temperature over time,
   wherein the second operation is maintained for a predetermined time after the two or more battery cells are discharged, and
   wherein the third operation is performed until the two or more battery cells are completely discharged.

2. The method according to claim 1, wherein the Joule heat is generated by current supplied from the two or more battery cells welded to the busbar.

3. The method according to claim 2, wherein the two or more battery cells are in a packed state before shipment.

4. The method according to claim 2, wherein whether the weld portion is defective is further determined based on a temperature decrease pattern of the weld portion when the heated weld portion is cooled by a cooling.

5. The method according to claim 4, wherein the cooling is performed by interrupting supply of the current from the two or more battery cells.

6. The method according to claim 4, wherein the temperature increase pattern is at least one of a time taken until the temperature of the weld portion reaches a specific temperature, a temperature increase rate over time of the weld portion, and a maximum temperature reached by the weld portion.

7. The method according to claim 4, wherein the temperature decrease pattern is at least one of a time taken until the temperature of the weld portion reaches an initial temperature from a predetermined temperature of the weld portion and a temperature decrease rate over time of the weld portion.

8. The method according to claim 4, wherein at least one of the temperature increase pattern and the temperature decrease pattern is set for the weld portion and a neighboring region of the weld portion, the weld portion and the neighboring region of the weld portion being divided into a predetermined number of regions.

9. The method according to claim 1, wherein the joule heat is represented by Equation 1, $$Q = I^2 \times R \times t, \qquad \text{Equation 1}$$

wherein Q is Joule heat, I is current through the weld portion, R is resistance of the weld portion, and t is time as current is applied.

10. The method according to claim 1, wherein the first operation forms the weld portions at a first surface of the welding lead portions of the two or more batteries while the busbar is contacting a second surface of the welding lead portions that is opposite to the first surface.

* * * * *